United States Patent
Orth et al.

(10) Patent No.: US 7,783,432 B2
(45) Date of Patent: Aug. 24, 2010

(54) METHOD FOR NONDESTRUCTIVE TESTING OF PIPES FOR SURFACE FLAWS

(75) Inventors: Thomas Orth, Mülheim/a.d. Ruhr (DE); Stefan Nitsche, Mülheim/a.d. Ruhr (DE); Till Schmitte, Bochum (DE)

(73) Assignee: V & M Deutschland GmbH, Düsseldorf (DE)

( * ) Notice: Subject to any disclaimer, the term of this patent is extended or adjusted under 35 U.S.C. 154(b) by 0 days.

(21) Appl. No.: 11/997,065

(22) PCT Filed: Jul. 28, 2006

(86) PCT No.: PCT/DE2006/001361
§ 371 (c)(1),
(2), (4) Date: Jan. 28, 2008

(87) PCT Pub. No.: WO2007/012331
PCT Pub. Date: Feb. 1, 2007

(65) Prior Publication Data
US 2008/0228412 A1    Sep. 18, 2008

(30) Foreign Application Priority Data

Jul. 29, 2005    (DE) ............... 10 2005 036 509
Jul. 29, 2005    (DE) ............... 10 2005 063 352
Jul. 27, 2006    (DE) ............... 10 2006 035 599

(51) Int. Cl.
*G01B 5/28*    (2006.01)
*G01N 27/82*    (2006.01)

(52) U.S. Cl. .................. 702/38; 324/238

(58) Field of Classification Search .......... 702/38, 702/33, 35, 36, 57–59, 81, 113, 115, 84, 702/108, 124, 126, 182, 183, 185, 188, 189, 702/190, 197; 324/207.2, 209, 219–222, 324/228, 234, 238, 259, 260, 263; 73/577, 73/578, 596, 618, 620, 622
See application file for complete search history.

(56) References Cited

U.S. PATENT DOCUMENTS 6,009,385 A    12/1999    Summerfield ............... 704/203

(Continued)

FOREIGN PATENT DOCUMENTS

DE    29 25 924 A1    1/1981

(Continued)

OTHER PUBLICATIONS

Yin et al., Real-Time Wavelet-Integrated Corrosion Detection System for Casing Pipes, 2000, Integrated Computer-Aided Engineering, vol. 7, No. 2, pp. 155-168.*

(Continued)

*Primary Examiner*—Michael P Nghiem
*Assistant Examiner*—Toan M Le
(74) *Attorney, Agent, or Firm*—Henry M. Feiereisen; Ursula B. Day

(57) ABSTRACT

A method for nondestructive testing of the pipes for detecting surface flaws using magnetic leakage flux is disclosed. With of the method, flaws can be detected and analyzed in near-real-time while the pipe is produced. The data obtained with inductive coils, Hall sensors or GMR sensors are digitized, the digital data are buffered in a first memory, and a subset of the digital data are copied into a second memory. The copied data are transformed with a wavelet transformation and the resulting wavelet coefficients are filtered and/or modified. In an alternative embodiment, the digital data can be continuously supplied to a routine for wavelet transformation, which is performed using cascaded digital signal processing routines. The evaluated variable is compared with a reference value, wherein a determined flaw-based signal can be unambiguously associated with the position of the flaw.

8 Claims, 2 Drawing Sheets

U.S. PATENT DOCUMENTS 6,382,029 B1 * 5/2002 Shoureshi et al. ............. 73/643
7,231,320 B2 * 6/2007 Papadimitriou et al. ..... 702/185

FOREIGN PATENT DOCUMENTS

| | | |
|---|---|---|
| DE | 102 25 344 A1 | 12/2003 |
| EP | 0 624 793 A | 11/1994 |
| EP | 0 834 845 A | 4/1998 |
| EP | 0 959 349 A2 | 11/1999 |

OTHER PUBLICATIONS

Afzal M. et al.: "Advanced signal processing of magnetic flux leakage data obtained from seamless gas pipeline" NDT & E International, Butterworth-Heinemann, Oxford, GB, vol. 35, No. 7, 2002, pp. 449-457, XP004378483, ISSN: 0963-8695, pp. 449-451.

* cited by examiner

METHOD FOR NONDESTRUCTIVE TESTING OF PIPES FOR SURFACE FLAWS

BACKGROUND OF THE INVENTION

The invention relates to a method for nondestructive testing of pipes for surface flaws.

Nondestructive methods for testing metal pipes for surface flaws, such as the magnetic leakage flux test, are known since some time and have proven to be reliable.

The DC field leakage flux test for detecting discontinuities disposed on the interior wall of a pipe is used for pipes made of ferromagnetic steel for detecting, in particular, longitudinally extending discontinuities near the surface, such as tears, scales or bulges.

Disadvantageously, the conventional evaluation methods used for the signals are not always capable of unambiguously detecting discontinuities disposed on the interior surface of pipes, in particular under unfavorable conditions for the wall thickness of the pipe and depth of the interior flaw, when a predetermined magnetization field intensity is applied. The separation between the flaw-based signal and the noise level is then too small to arrive at meaningful results. It then becomes necessary to employ, as described below, novel filtering techniques based on wavelet algorithms.

Magnetic leakage flux signals are measured with inductive coils, Hall sensors or GMR sensors. These signals always include a certain amount of noise and have a slowly varying background. When using conventional noise reduction, the signal noise is reduced with an analog filtering technique and the slowly varying components are suppressed with a difference technique. The analog filtering technique quickly reaches its limits, because the flaw-based signals due to magnetic leakage flux often appear in a similar frequency range as the interfering signals from the background. There is also a risk that signals of interest, which should actually be displayed, are filtered out with difference techniques.

It would therefore be desirable to investigate alternative filtering techniques. In addition to digital filtering with conventional filtering algorithms, the so-called wavelet algorithms are particularly suited for this task. Instead of harmonic functions, wavelets are used as filter criteria because these can be very similar to the useful signals. With wavelet filters, noise can be much more effectively reduced than with conventional filtering techniques.

It is generally known, for example from DE 102 25 344 A1, to use a wavelet transformation for evaluating time-dependent signals in industrial process monitoring to separate the noise components of the signals from the information components of the signals. In a wavelet transformation, which is an extension of the Fourier transformation, the original signal is projected onto wavelet basic functions, which corresponds to a transformation from the time domain to the time-frequency plane. The wavelet functions which are localized in the time domain and in the frequency domain, are derived from a single prototype wavelet, the so-called mother function, by dilatation and translation.

The intent is here to significantly reduce with the wavelet transformation the noise level compared to the signal caused by the flaw.

The conventional method discloses in general terms the advantages of applying of the wavelet algorithm to noise suppression for monitoring industrial processes. It is imperative with pipes produced in a continuous production process that the signals from the nondestructive testing are analyzed in near-real-time, so as to be able to immediately change the production process when flaws occur (for example, correlating the flaw by marking the pipe section or stopping the production process). However, DE 102 25 344 A1 does not address this issue.

Therefore, a persistent problem in leakage flux testing is that surface test data of pipes must be measured and processed in near-real-time so as to allow intervention in the ongoing production process when flaws occur.

It is an object of the invention to provide a reliable and cost-effective method and a device for nondestructive testing of pipes using leakage flux, which can be used to measure and process the data related to surface flaws in the pipe in near-real-time by using a wavelet transformation.

SUMMARY OF THE INVENTION

The object of the invention is attained for leakage flux testing in that near-real-time measurement and evaluation are performed with the following steps:

transmitting the signals to a pre-amplifier, converting the analog signals into a continuous data stream of digital data, buffering the data stream in a first memory (A), filling the first memory (A) with k data points, copying the k data points from the first memory (A) into a second memory (B) within a short time interval between two digital data points and simultaneously refilling the first memory (A) with new data, transforming the copied data with a wavelet transformation and filtering or modifying, or both, the resulting wavelet coefficients, comparing the valuation variable with a reference value, wherein a determined flaw-based signal can be unambiguously associated with the position of the flaw.

Likewise, the invention is attained according to claim 6 with the following steps:

transmitting the signals to a pre-amplifier, converting the analog signals into a continuous data stream of digital data, continuously supplying the data to a routine for wavelet transformation, performing the wavelet transformation with a cascade of digital signal processing routines, comparing the valuation variable with a reference value, wherein a determined flaw-based signal can be unambiguously associated with the position of the flaw.

BRIEF DESCRIPTION OF THE DRAWING

The invention will now be described in more detail with reference to the accompanying drawing, in which.

DETAILED DESCRIPTION OF PREFERRED EMBODIMENTS

Figure 1:
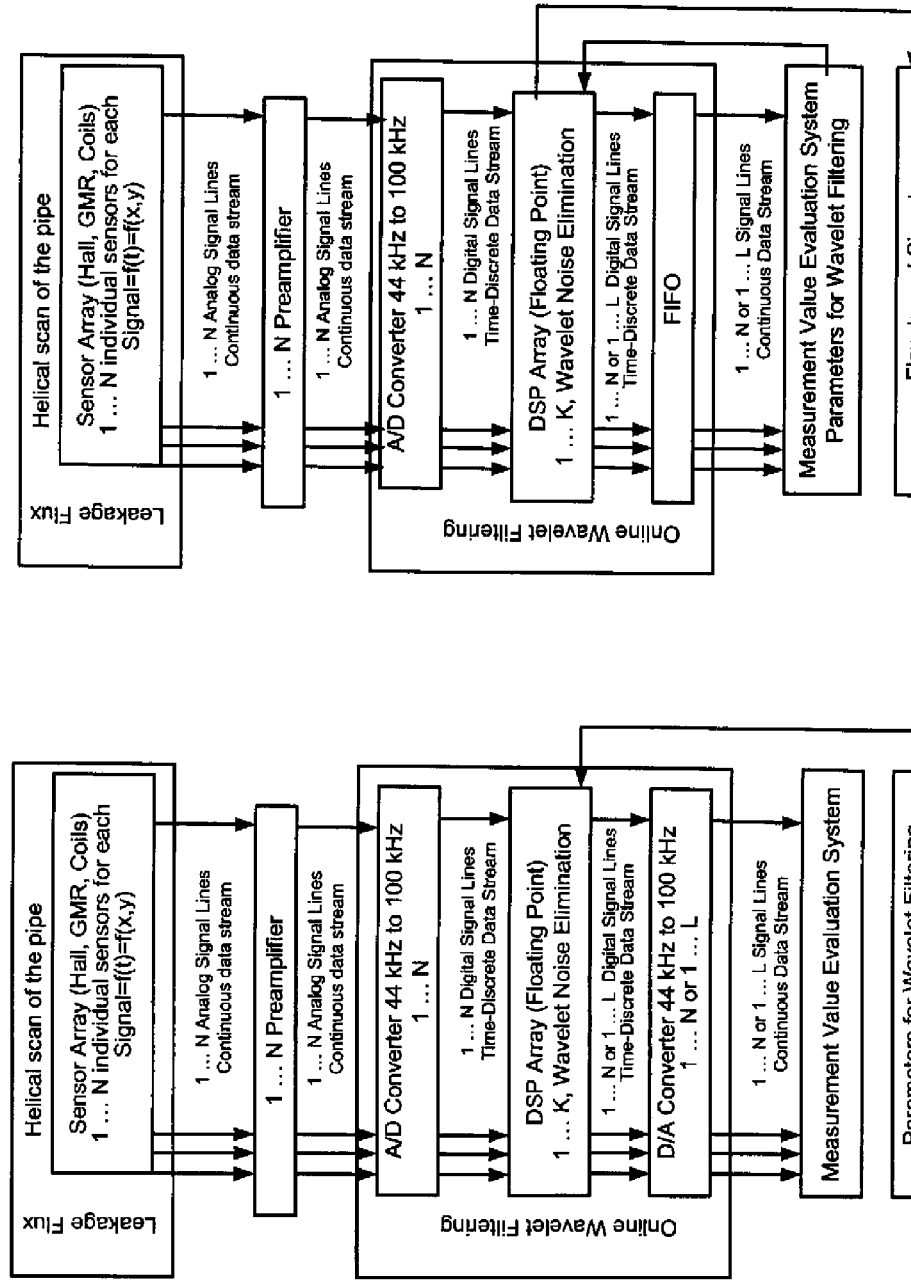
FIG. 1 is an exemplary embodiment, showing a flow chart on the left side of a first variant of a signal pattern, and on the right side a flow chart of a second variant of a signal pattern.

Turning now to FIG. 1, there is shown a flow chart on the left side of a first variant of a signal pattern, and on the right side a flow chart of a second variant of a signal pattern.

The variant 1 illustrated on the left side describes the signal pattern of a single channel for near-real-time signal processing in leakage flux testing, and an analog input and output found, for example, in existing systems.

The leakage flux signals are measured using inductive coils, Hall sensors or GMR sensors. A continuous analog signal current is provided downstream of the sensors and the connected pre-amplifiers. The frequency content and the signal level are determined by the transmission characteristics of the pre-amplifiers.

The A/D converter transforms the analog signal into a continuous data stream of digital data (time-discrete signal). Due to the Nyquist theorem, the maximal frequency is defined as half the sampling rate. The sampling rate also limits the spatial resolution of the leakage flux signal.

The data stream is a buffered in a first memory (A) (not shown in the Figure). As soon as the first memory is filled with k data points (typically: k=512 or 1024), the content is copied to a second memory (B) which performs a filtering operation with the actual wavelet transformation.

The data are copied within a short time between two digital data points, so that after the data are copied from the first memory (A) to the second memory (B), new data can be written into the first memory (A).

Advantageously, after filtering, the filtered data of the second memory (B) are copied into a third memory (C).

The filtered signals are outputted from the third memory (C) with the same clock rate used to fill the first memory (A), so that there is always an identical number of input data and output data.

With this method, the time required for filtering is less than the time required by the system for filling or emptying the input and output memory, respectively.

With this method, the signal sequence is temporally offset by exactly k data points.

The output signals of the third memory (C) are converted again by a D/A converter with a smoothing stage into a continuous analog measurement signal which can be supplied to an existing analog data acquisition system. It should be taken into account that the level and frequency dependence of the signal are determined by the D/A module, whereas an optional matching is attained by an additional amplifier component.

In another embodiment of the filtering system for leakage flux signals, the data are not processed in blocks of k data points (as described above), but the filter operates so fast that the execution time is shorter than the time interval between the arrival of the data points. The filter can then always be executed with the last k data points, thereby obtaining one filtered data point for each incoming data point.

With this method, the temporal offset between input and output data is at most one data point. Also feasible are mixed solutions of the two afore-described methods: in this case, blocks of data points with decreasing size are collected (e.g., with i points), and the filter is executed always with the last h blocks, so that the number of points in the wavelet filter is once more k=i*h.

The variant 2 illustrated on the right side of FIG. 1 describes the signal pattern for near-real-time signal processing in a leakage flux test and an analog input and a digital output, as contemplated for the novel embodiment of leakage flux test systems according to the invention.

In this case, the data are supplied to the digital signal processor (DSP) in accordance with the afore-described methods, without the need for a subsequent D/A conversion. The filtered data in memory (C) (not illustrated in the Figure) can then be supplied in digital form directly to a supervisory data processing system.

In another advantageous embodiment, the flaws can be evaluated and the signals can be processed further directly on the DSP.

The above discussions relating to the variants 1 and 2 apply in principle also to all additional signal channels; however, the filtered signals can already be combined on the DSP and several channels can be compared, for example, by computing several channels on a DSP or by sequentially cascading several DSPs. As a result, the N signal lines for the N channels may be converted into L signal lines (with L<N, e.g., L=N/2).

Figure 2:
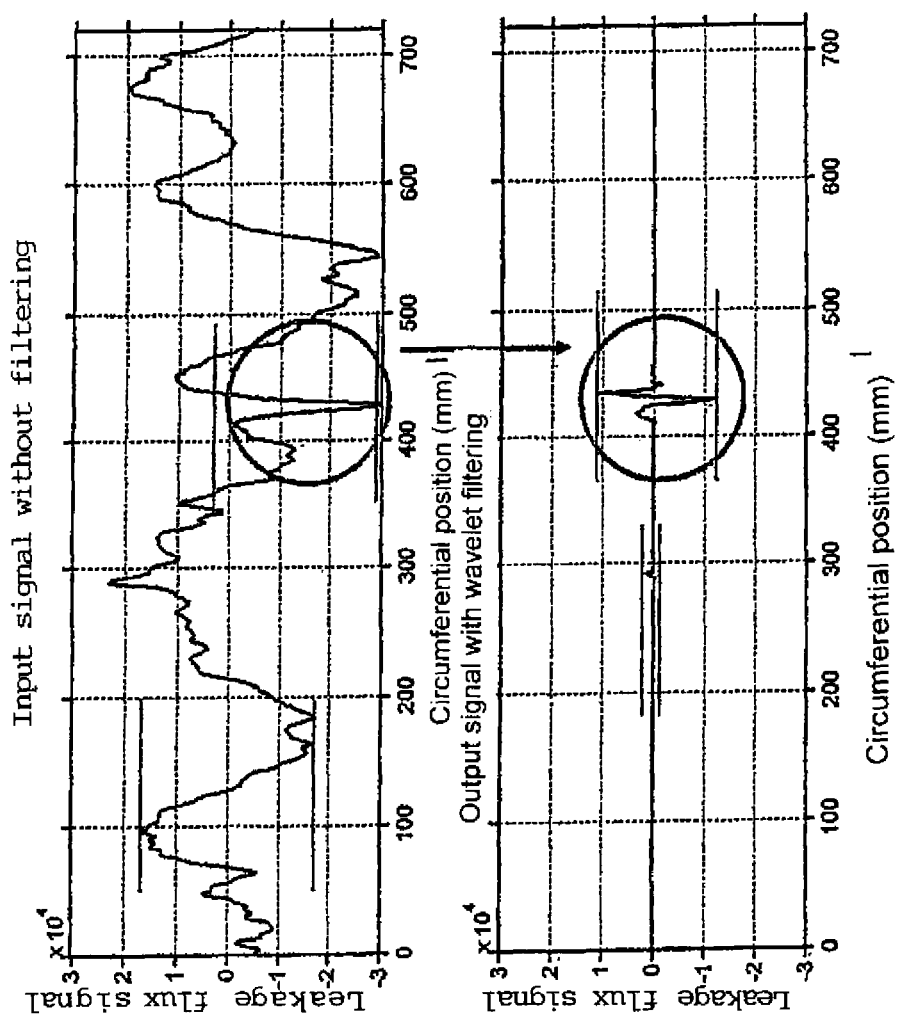
FIG. 2 is an exemplary diagram of a measurement signal of a leakage flux test.

FIG. 2 shows an exemplary diagram of a leakage flux test for flaws located on the interior surface of a pipe.

The upper section of the diagram shows the pattern of the measured leakage flux signal without filtering. A possible flaw-based signal in the signal pattern cannot be unambiguously determined.

The lower part of the diagram shows the flaw-based signal from an interior flaw which has been filtered from the leakage flux signal by the wavelet transformation, wherein the flaw-based signal is displayed depending on the preset threshold values.

What is claimed is:

1. A method for near-real-time nondestructive testing of pipes made of a magnetizable material for flaws based on leakage flux, comprising the steps of:

moving a pipe longitudinally or rotationally, or both, generating a magnetic flux and transferring the magnetic flux contactless into the pipe, scanning the pipe in a helical pattern, detecting with one or more sensors a magnetic leakage flux exiting from a surface of the pipe, said magnetic leakage flux produced by discontinuities located in a region near the pipe surface, converting the detected magnetic leakage flux in near-real-time into processable electrical analog signals, transmitting the analog signals to a pre-amplifier, converting the analog signals into a continuous data stream of digital data, continuously supplying the data from the data stream to a routine for wavelet transformation, performing the wavelet transformation with cascaded digital signal processing routines to produce continuous streams of wavelet coefficients, comparing an evaluation parameter derived from the wavelet coefficients with a reference value to produce a flaw-based signal, associating the flaw-based signal with a position of the flaw, filtering or modifying, or both, the continuous streams of wavelet coefficients, back-transforming the filtered or modified wavelet coefficients into a stream of continuous data by applying an inverse of the cascaded digital signal processing routines, converting the stream of continuous data with a D/A converter into a continuous analog measurement signal, and supplying the measurement signal to an existing analog data acquisition system.

2. The method of claim 1, further comprising the step of buffering the continuous data stream in a first memory.

3. The method of claim 1, further comprising the step of buffering the stream of continuous data in a second memory.

4. The method of claim 3, wherein the buffered stream of continuous data is outputted from the second memory with a clock rate that is identical to a clock rate used to fill the first memory.

5. The method of claim 1, further comprising the step of directly supplying the stream of continuous data to a digital computing unit or a supervisory data processing system.

6. The method of claim 5, wherein the digital computing unit is a digital signal processor (DSP).

7. The method of claim 1, wherein the continuous analog measurement signal is copied into a third memory and converted into a smoothed continuous analog measurement signal.

8. The method of claim 1, further comprising the steps of determining suitable wavelet basic functions that are matched to signals of the leakage flux, and filtering the wavelet coefficients with the determined wavelet basic functions.

* * * * *